United States Patent
Roszkowiak et al.

(10) Patent No.: US 11,103,260 B2
(45) Date of Patent: Aug. 31, 2021

(54) FECAL IMPACTION REMOVAL DEVICE

(71) Applicant: Medline Industries, Inc., Northfield, IL (US)

(72) Inventors: Amanda Roszkowiak, Schaumburg, IL (US); Derrick Roemisch, McHenry, IL (US); Donald J. Propp, Dewitt, MI (US)

(73) Assignee: Medline Industries, Inc., Northfield, IL (US)

( * ) Notice: Subject to any disclaimer, the term of this patent is extended or adjusted under 35 U.S.C. 154(b) by 164 days.

(21) Appl. No.: 16/515,430

(22) Filed: Jul. 18, 2019

(65) Prior Publication Data

US 2021/0015505 A1 Jan. 21, 2021

(51) Int. Cl.
*A61B 17/22* (2006.01)
*A61M 29/00* (2006.01)
*A61M 3/02* (2006.01)

(52) U.S. Cl.
CPC ............. *A61B 17/22* (2013.01); *A61M 29/00* (2013.01); *A61B 2017/22037* (2013.01); *A61M 3/02* (2013.01)

(58) Field of Classification Search
CPC ......... A61B 17/22; A61B 2017/22037; A61M 3/02; A61M 3/0204; A61M 3/0208; A61M 3/0212; A61M 3/0216; A61M 3/0233; A61M 3/0279; A61M 3/0291; A61M 29/00; A61M 29/02; A61M 31/00
See application file for complete search history.

(56) References Cited

U.S. PATENT DOCUMENTS

| | | | |
|---|---|---|---|
| 24,957 A | 8/1859 | Shogren | |
| 833,759 A | 10/1906 | Sourwine | |
| 1,383,502 A | 7/1921 | Vultee | |
| 1,401,675 A | 12/1921 | Cooper | |
| 1,737,488 A | 11/1929 | Zohlen | |
| 1,828,986 A | 10/1931 | Stevens | |
| 1,972,428 A | 9/1934 | Richard | |
| 3,022,787 A | 2/1962 | Daniel | |
| 3,459,175 A * | 8/1969 | Miller | A61M 31/00 600/431 |
| 3,659,611 A | 5/1972 | Miller | |
| 3,842,834 A | 10/1974 | Vass | |
| 3,889,676 A | 6/1975 | Greene | |

(Continued)

FOREIGN PATENT DOCUMENTS

| | | |
|---|---|---|
| AU | 200079397 | 4/2001 |
| CA | 2261419 | 8/2000 |

(Continued)

*Primary Examiner* — Jocelin C Tanner
(74) *Attorney, Agent, or Firm* — Fitch, Even, Tabin & Flannery LLP

(57) ABSTRACT

A fecal impaction removal device includes an elongated shaft extending along a central longitudinal axis. A dilation body is secured at a distal end of the elongated shaft for insertion into a rectum of a patient. The dilation body has a maximum radial extension in a direction orthogonal to the central longitudinal axis. The fecal impaction removal device includes a stop member that extends from a central region of the elongated shaft. The stop member has a length along a major axis that is greater than the maximum radial extension of the dilation body.

18 Claims, 10 Drawing Sheets

(56) References Cited

U.S. PATENT DOCUMENTS

| | | | |
|---|---|---|---|
| 3,894,539 A | 7/1975 | Tallent | |
| 3,938,514 A | 2/1976 | Boucher | |
| 4,014,332 A | 3/1977 | Sneider | |
| 4,243,037 A | 1/1981 | Smith | |
| 4,921,484 A | 5/1990 | Hillstead | |
| 4,964,852 A | 10/1990 | Dunning | |
| 5,129,910 A | 7/1992 | Phan | |
| 5,702,404 A | 12/1997 | Willingham | |
| 5,730,726 A | 3/1998 | Klingenstein | |
| 5,827,304 A | 10/1998 | Hart | |
| 5,976,170 A | 11/1999 | Levin | |
| 6,138,984 A | 10/2000 | Abell | |
| 6,395,021 B1 | 5/2002 | Hart | |
| 6,419,673 B1 | 7/2002 | Edwards | |
| 6,902,557 B2 * | 6/2005 | Mezzoli | A61M 3/0262 604/514 |
| 8,016,816 B2 | 9/2011 | Gregory | |
| 8,105,335 B1 * | 1/2012 | Bentley | A61M 3/02 606/127 |
| 8,353,860 B2 | 1/2013 | Boulais | |
| 8,491,526 B2 | 7/2013 | Cronin | |
| 8,574,206 B2 * | 11/2013 | Bjerregaard | A61F 5/442 604/328 |
| 8,579,857 B2 | 11/2013 | Haack | |
| 8,579,914 B2 | 11/2013 | Menn | |
| RE46,306 E | 2/2017 | Bentley, II | |
| 2003/0130629 A1 | 7/2003 | Cherepanov | |
| 2004/0039348 A1 * | 2/2004 | Kim | A61M 3/0241 604/264 |
| 2005/0165412 A1 | 7/2005 | Secrest | |
| 2005/0197644 A1 | 9/2005 | Waychoff, II | |
| 2005/0256464 A1 | 11/2005 | Pallas | |
| 2007/0005001 A1 | 1/2007 | Rowe | |
| 2008/0045881 A1 | 2/2008 | Teitelbaum | |
| 2008/0269754 A1 * | 10/2008 | Lutz | A61B 17/1626 606/79 |
| 2008/0300619 A1 * | 12/2008 | Isham | A61M 29/02 606/197 |
| 2010/0042107 A1 | 2/2010 | Merrifield | |
| 2011/0054413 A1 * | 3/2011 | Romhild | A47K 7/08 604/212 |
| 2011/0092892 A1 | 4/2011 | Nitsan | |
| 2012/0253284 A1 | 10/2012 | Nitsan | |
| 2020/0178988 A1 * | 6/2020 | Henry | A61M 3/0233 |

FOREIGN PATENT DOCUMENTS

| | | |
|---|---|---|
| DE | 2941743 | 4/1981 |
| DE | 202004015357 | 1/2005 |
| EP | 109897 | 5/1984 |
| EP | 0525110 | 6/1997 |
| WO | 2008117320 | 10/2008 |
| WO | 2011018092 | 2/2011 |
| WO | 2012004118 | 1/2012 |

* cited by examiner

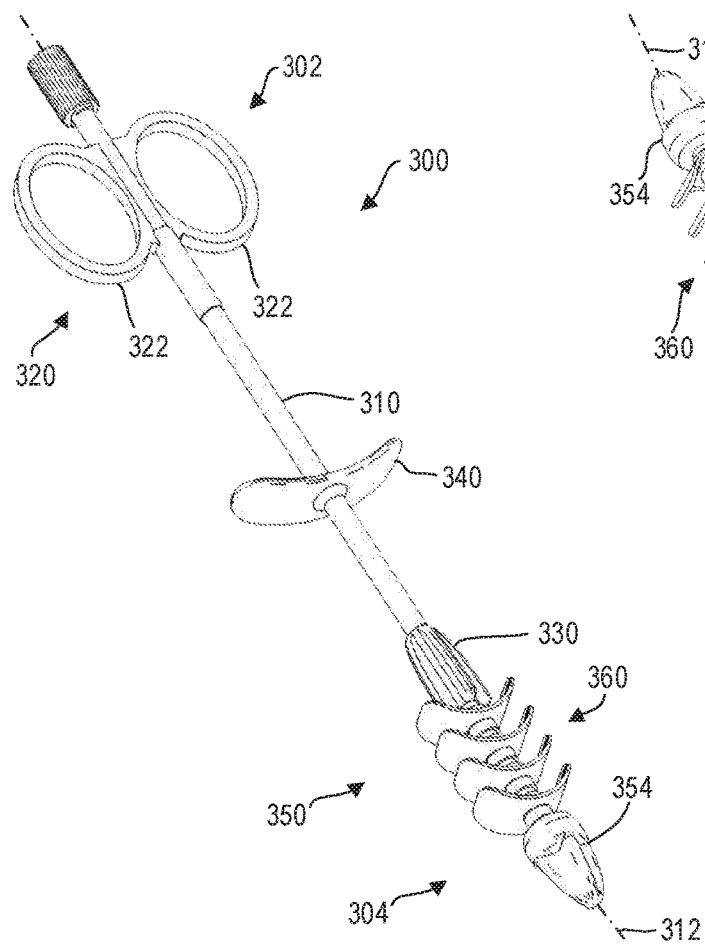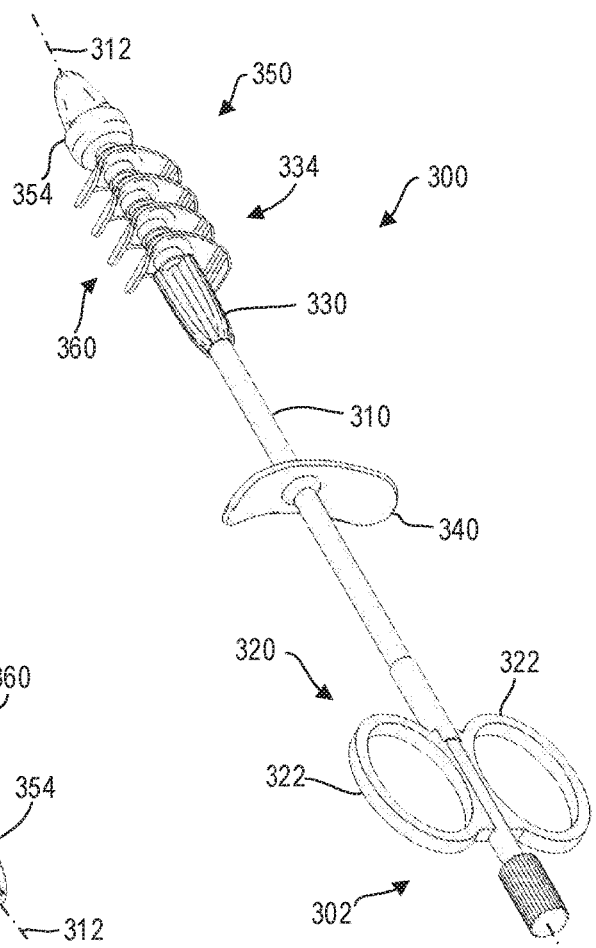
FIG. 18  FIG. 19
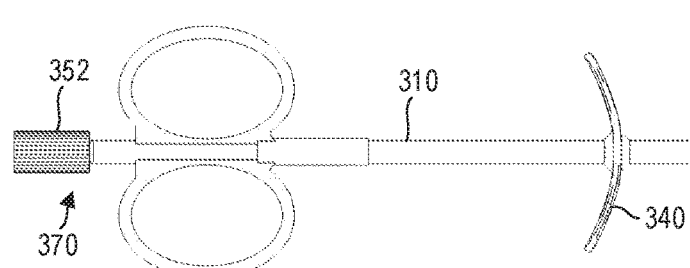
FIG. 20
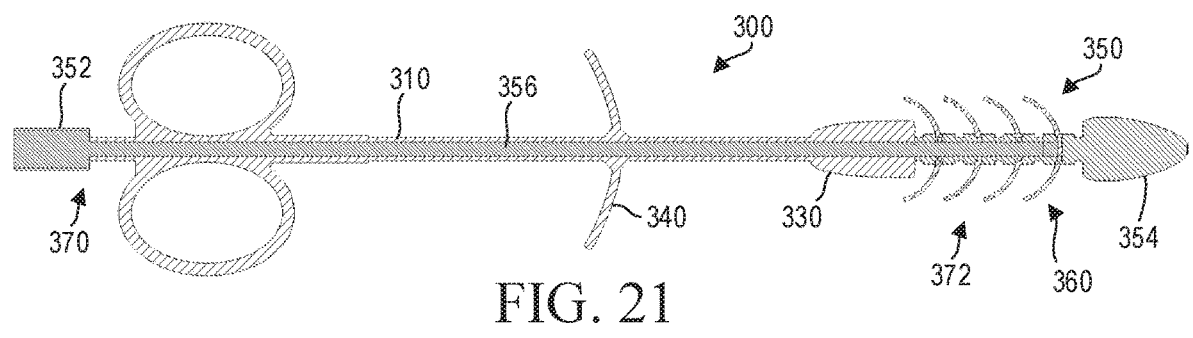
FIG. 21

FECAL IMPACTION REMOVAL DEVICE

TECHNICAL FIELD

This disclosure relates generally to devices for removal of fecal impactions and more particularly to such devices including dilators and safety features.

BACKGROUND

Patients often present in clinical settings with impacted stools. Impacted stools may be caused by blockages that may result from the inability to empty the rectum of accumulated stool. Such blockages, referred to as fecal impactions, may occur due to excessive and continuing fecal mass accumulation in the rectal vault such that the large and growing fecal bolus is not readily passed through the anus. A fecal impaction may worsen as additional stool is produced, and may harden with drying of distal portions of the impacted stool.

In many instances, medical intervention is required for removal of a fecal impaction from the rectum. In one approach, a medical practitioner repeatedly inserts their finger through the anus and into the rectum of a patient in an effort to manually dislodge the stool mass either entirely or in fragments. Such manual manipulation is often insufficient to relieve the impaction condition, as the practitioner may not be able to grasp the fecal mass or to gain attachment thereto due to the shape of a finger and the inability to frictionally engage the mass. Probing of the fecal mass with the finger of a clinician involves blind sweeps and stirring motions that are not easily directed and can prove ineffective. Patient discomfort is often increased by attempts of the attending clinician to curl the inserted finger in an effort to improve connection with the fecal mass. This flexion motion often causes further distention of an already distended bowel. Pain thus often accompanies inefficiency during attempts to remove the impaction and may require the practitioner to abort the procedure.

In other approaches, various devices may be used to remove a fecal impaction. For example, a fecal impaction removal tool is disclosed in U.S. Pat. No. 8,105,335, which is hereby incorporated by reference as if fully set forth herein.

In many instances, a practitioner may have difficulty judging a depth of the distal end of such a device within the rectum of a patient. If a device is inserted too far into the rectum, the risk of perforation or other harm to the patient is greatly increased. Accordingly, there is a need for a fecal impaction removal tool that is better optimized in terms of indicating depth of insertion. Furthermore, there is a need for a fecal impaction removal tool having a feature that prevents or restricts a practitioner from inserting the tool too far into the rectum of a patient.

SUMMARY

In one approach, a fecal impaction removal device includes an elongated shaft that extends along a central longitudinal axis, a dilation body, and a stop member. The elongated shaft, the dilation body, and the stop member may be unitary and integrally formed. In this way, the elongated shaft, the dilation body, and the stop member may have a common shore "A" durometer value. In at least one approach, the elongated shaft includes a substantially hollow central channel that extends through the stop member.

The dilation body may be disposed at a distal portion of the elongated shaft for insertion into a rectum of a patient, and may have a maximum radial extension in a direction orthogonal to the central longitudinal axis. In one approach, the dilation body is a tapered dilation body that has a tapered surface and a tapering helical band that extends about the central longitudinal axis along the tapered surface.

The stop member may extend from a central portion of the elongated shaft, and may have a length along a major axis that is greater than the maximum radial extension of the dilation body. The stop member may be a generally obround stop member that includes diametrically opposed fin portions that generally extend along the major axis. In one aspect, the stop member is a curved stop member. For example, the stop member may include a convex distal surface that faces the dilation body and curves in a direction away from the dilation body as the stop member extends radially away from the central longitudinal axis. The length of the stop member may be greater than the maximum radial extension of the dilation body by at least a factor of two.

According to one aspect, the fecal impaction removal device further includes a proximal dilator and a handle. The stop member may be disposed axially between the proximal dilator and the handle.

According to another aspect, the fecal impaction removal device further includes a plurality of compressible grappling elements and a handle. The stop member may be disposed axially between the compressible grappling elements and the handle. Furthermore, the length of the stop member along the major axis may be greater than a length of an individual compressible grappling element.

According to another approach, a fecal impaction removal device includes an elongated shaft that extends along a central longitudinal axis. The fecal impaction removal device further includes a dilation body that is disposed at a distal end of the elongated shaft for insertion into a rectum of a patient. The dilation body includes a tapering body portion and a tapering helical band that extends about tapering body portion along the central longitudinal axis.

In one aspect, the tapering helical band has a varying outer diameter about the central longitudinal axis as the tapering helical band extends along the central longitudinal axis. For example, the tapering helical band may have a first radial height from the central longitudinal axis at a distal end of the dilation body, and a second radial height from the central longitudinal axis at a proximal end of the dilation body. The second radial height may be greater than the first radial height. Furthermore, the first radial height of the tapering helical band may be less than a radial height of the tapering body portion at the proximal end of the dilation body.

In one approach, the fecal impaction removal device includes a curved generally obround stopper disposed at a central region of the elongated shaft.

The fecal impaction removal device may include a bulbous depth indicator disposed at a central region of the elongated shaft. The bulbous depth indicator may be colored an indicator color that is different than a color of the elongated shaft.

According to another approach, a fecal impaction removal device includes an elongated shaft having a proximal portion, a distal portion opposite the proximal portion, and a substantially hollow central channel that extends along a central longitudinal axis between the proximal portion and the distal portion. The fecal impaction removal device may further include an actuating rod that extends through the central channel and is rotatable relative to the elongated shaft.

The fecal impaction removal device may further include a tapered dilation body that is rotatably fixed to a distal end of the actuating rod such that rotation of the actuating rod effects a rotation of the tapered dilation body relative to the elongated shaft. The tapered dilation body may be shaped for insertion into a rectum of a human. In one approach, the dilation body includes a tapering body portion and a tapering helical band that extends about tapering body portion along the central longitudinal axis.

In one aspect, the fecal impaction removal device includes a stop member that extends from a central portion of the elongated shaft. The stop member may have a length along a major axis that is greater than a maximum radial extension of the tapered dilation body.

BRIEF DESCRIPTION OF THE DRAWINGS

FIG. 18 is a perspective view of a fifth impaction removal device shown from a distal end.

FIG. 19 is a perspective view of the fifth fecal impaction removal device shown from a proximal end.

FIG. 20 16 is a side elevation view of the fifth fecal impaction removal device.

FIG. 21 is a side elevation cross-sectional view of the fifth fecal impaction removal device.

DETAILED DESCRIPTION

Figures 1, 2:
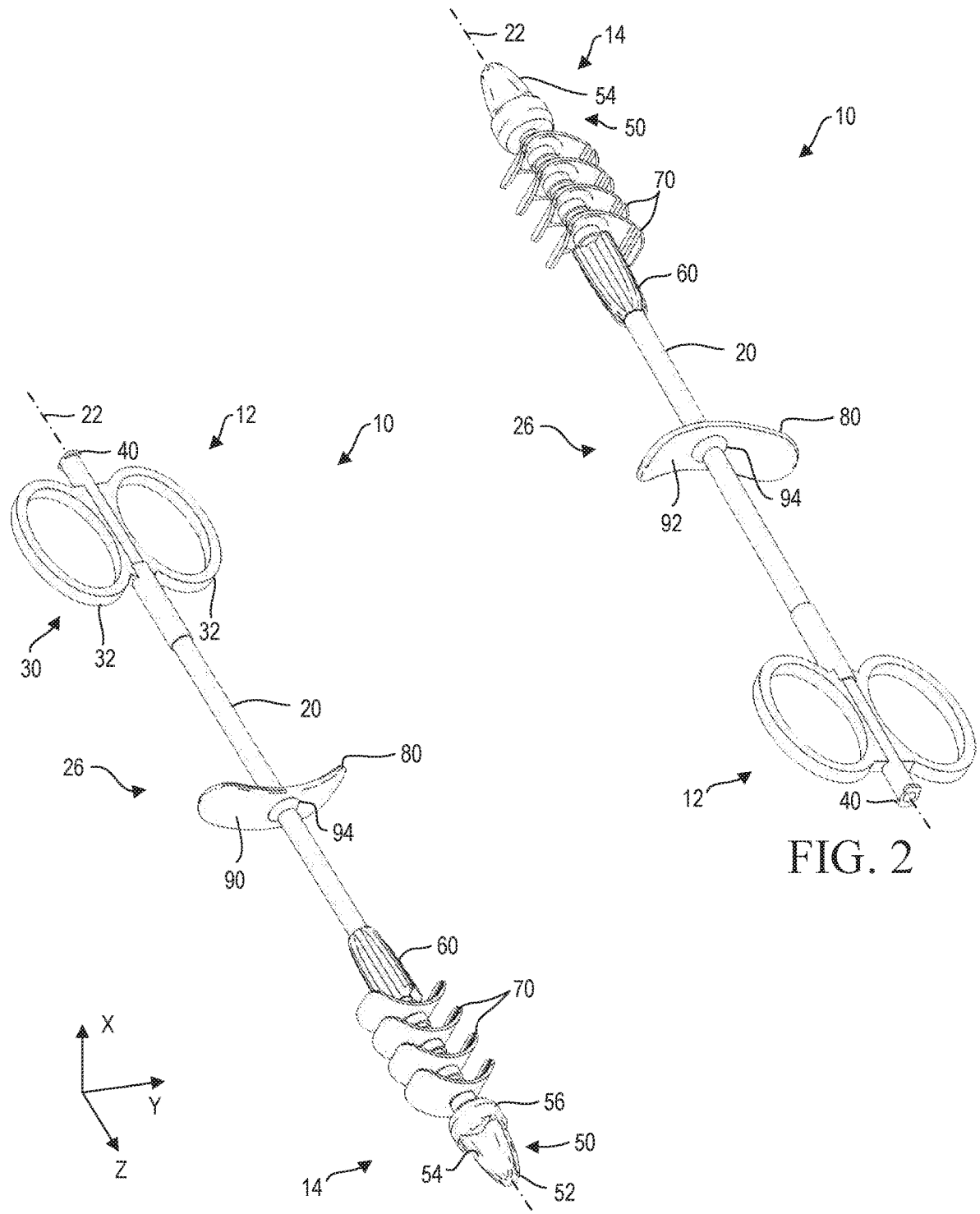
FIG. 1 is a perspective view of a first impaction removal device shown from a distal end.
FIG. 2 is a perspective view of the first fecal impaction removal device shown from a proximal end.

Embodiments of the present disclosure are described herein. It is to be understood, however, that the disclosed embodiments are merely examples and other embodiments may take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the present invention. As those of ordinary skill in the art will understand, various features illustrated and described with reference to any one of the figures may be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Referring now to FIGS. 1-6, a fecal impaction removal device 10 includes a proximal portion 12 that a medical practitioner can grasp, and a distal portion 14 opposite the proximal portion 12 that is configured to be inserted through the anus of a patient and into the rectal vault to engage an impacted fecal mass lodged therein.

The fecal impaction removal device 10 includes a shaft 20, which may be an elongated shaft, that extends along an axis, referred to herein as a central longitudinal axis 22, between the proximal portion 12 and the distal portion 14. The shaft 20 may be formed of a resinous or plastic material and is sufficiently rigid to allow partial insertion of the device 10 into the rectum as well as manipulation of the device 10 while engaged with an impaction, followed by withdrawal to remove at least fragments of an impaction created by manipulation of the device 10.

The device 10 includes a handle 30 at the proximal portion 12 of the device 10 (e.g., at a proximal end of the shaft 20). At least a portion of the handle 30 may be integrally formed with the shaft 20, or may be separately formed and secured to the shaft 20. In the approach shown, the handle 30 is formed of loops 32 that are each capable of receiving one or more of a practitioner's fingers for ease of use of the device 10. The loops 32 may facilitate manipulation of the device 10, and may assist in withdrawal of the device 10 from the patient. Manipulation of the device may include an application of torque by a practitioner manually grasping the loops 32 of the handle 30 and/or a series of small inward and outward displacements of the device 10. The loops 32 are disposed in opposed relation and are dimensioned to prevent entry of the entire device 10 into the anus to prevent "loss" of the device 10 into the rectum.

In one aspect, the shaft 20 terminates at its proximal end in a locking adaptor 40, which may be in the form of a Luer lock. The locking adaptor 40 is disposed at the proximal end of a lumen 42 that extends through the shaft 20 internally thereof, thereby forming a channel within the shaft 20. In this way, the shaft 20 may be hollow, or substantially hollow, from the proximal end inwardly toward a distal end of said shaft 20. The lumen 42 serves as a conduit for delivery of fluids such as enema fluids under pressure. The locking adaptor 40 facilitates connection to an apparatus (not shown) capable of delivering enema fluids into the lumen 42. Such apparatus can include a syringe or other device capable of being coupled to the proximal end of the shaft 20 for delivery of an enema fluid into the lumen 42. The fluids thus introduced into the interior of the hollow shaft 20 are chosen for facilitation of stool softening, lubrication and/or mechanical absorption of an impacted fecal mass disposed in a patient's rectum. Such fluids can be introduced concurrently with or independently of manipulation of an impaction such as prior to intended manipulation.

In one approach, the shaft 20 is formed with ports 44 disposed in spaced relation along the shaft 20 at locations along the shaft 20 near the distal end of the shaft 20. The ports 44 communicate the lumen 42 with an impaction or with the interior of the rectal vault so that enema solution introduced as into the hollow shaft 20 is directed toward an impacted fecal mass to facilitate softening and/or fragmentation of the mass either prior to or during manipulation of the device 10. The ports 44 may be formed in the shaft 20 in pairs, with one each of the ports 44 in a pair of ports being located oppositely across the width or diameter of the shaft 20. As further described herein, the ports 44 are typically disposed immediately adjacent to and proximally of sets of flexible, arcuately configured grappling elements formed on the shaft 20.

In still another approach, the device 10 includes a solid shaft that does not define a hollow lumen therein. In such an approach, the distal portion 14 of the device 10 may be provided without ports.

The shaft 20 terminates distally in a first or distal dilation body, also referred to herein as dilator 50. In one approach, the dilator 50 is formed integrally with the shaft 20. In another approach, the dilator 50 is separately formed and secured to the shaft 20.

The dilator 50 has a substantially ogive conformation with a rounded tip 52. The dilator 50 is formed distally in a cruciform configuration from a plurality of regularly spaced elements 54 that taper toward the tip 52 and join proximally to a substantially circular base 56 joined to the shaft 20. The dilator 50 may define a maximum outer diameter 58 at the substantially circular base 56. The maximum outer diameter 58 may correspond to a maximum distance that the dilator 50 extends away from the central longitudinal axis 22 in the X-Y plane.

The elements 54 as well as surfaces of the base 56 are relieved, that is, essentially rounded such that the dilator 50 can be inserted into and withdrawn from a patient's anus with ease and with minimal discomfort to the patient. The dilator 50 can be lubricated prior to insertion. The dilator 50 is shaped and sized such that insertion minimally distends an impacted fecal mass as well as the rectal vault to minimize patient discomfort.

In one aspect, the dilator 50 has an axial length in the range of approximately 20 millimeters to approximately 30 millimeters (e.g., 25 millimeters).

The device 10 further includes a second or proximal dilation body, referred to herein as dilator 60. In one approach, the dilator 60 is formed integrally with the shaft 20. In another approach, the dilator 60 is separately formed and secured to the shaft 20.

The proximal dilator 60 is disposed in spaced relation to the distally disposed dilator 50. The dilator 60 is conically shaped proximally to facilitate removal of the device 10 once manipulation of an impacted fecal mass has occurred. The dilator 60 can be formed with smooth, low friction surfaces over the exterior thereof and can be formed in a cruciform configuration as is the dilator 50 is formed distally except with such cruciform shape extending in the direction of withdrawal of the device 10. The dilator 60 is intended to be received through the anus of a patient during insertion of the device 10 and is therefore configured with an inwardly rounded annular shoulder formed distally of the dilator 60. The dilator 60 facilitates the atraumatic withdrawal of the device 10 through dilation of the anus and relaxation of the anal sphincter. Such relaxation and dilation permit withdrawal of at least portions of an impacted fecal mass engaged with the device 10 with minimal effort and with minimal discomfort to the patient.

The device 10 further includes one or more grappling elements 70. The grappling elements 70 may be flexible, arcuately configured grappling elements 70. As shown, the device includes four grappling elements 70 disposed in spaced axial relation between the distally disposed dilator 50 and the proximal dilator 60. The number of the grappling elements 70 used in a particular tool can vary and be other than is shown herein. In the approach shown, the grappling elements 70 have aligned orientations. However, grappling elements 70 may also or instead be provided in angularly-offset orientations.

An individual grappling element 70 includes a substantially straight-edged inner body portion having arcuate perimetric portions at each end of said body portion. The grappling elements 70 are preferably formed on and about the shaft 20 by co-extrusion of a plastic or resinous material of lesser durometer than that of the shaft 20 during formation of the device 10. The material forming the grappling elements 70 are thus preferably formed of a "softer" material to allow flexure of a sufficient degree to permit each grappling element 70 of each arcuately-shaped set to bend inwardly toward the shaft 20 upon insertion of the device 10 into the anus of a patient. The grappling elements 70 can bend sufficiently to compress inwardly to positions such that the perimetric portion of each grappling element 70 lies along the shaft 20. In this way, the grappling elements 70 do not need to create an entry path into the anus or into an impacted fecal mass. However, on full receipt into the fecal mass, a compressing pressure on the grappling elements 70 is released due to restoring spring-like forces provided by the grappling elements 70 and/or by manipulation of the device 10 in one or more series of short inward and outward movements of the device 10. The grappling elements 70 thus extend outwardly of the shaft 20 during engagement with a fecal mass to positions similar to those existing prior to insertion. The fecal mass is thus engaged by the grappling elements 70 in a "hooking" action and can be fragmented while embedded within the mass. Ridges formed on rearwardly facing surfaces of the grappling elements 70 act to increase retention of at least portions of the fecal mass on the device 10.

Figure 3:
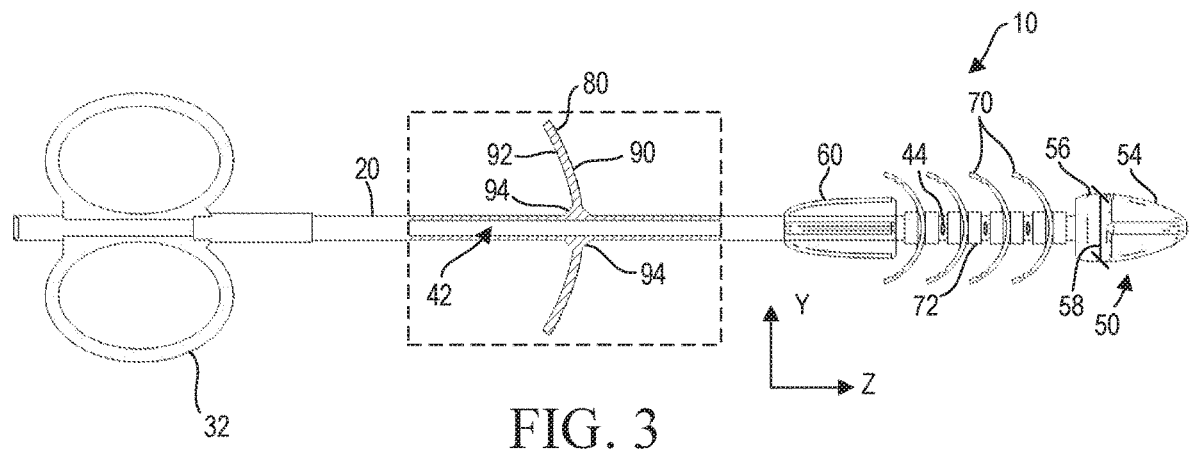
FIG. 3 is a top plan view of the first fecal impaction removal device with a portion shown in cross-section.
Figure 4:
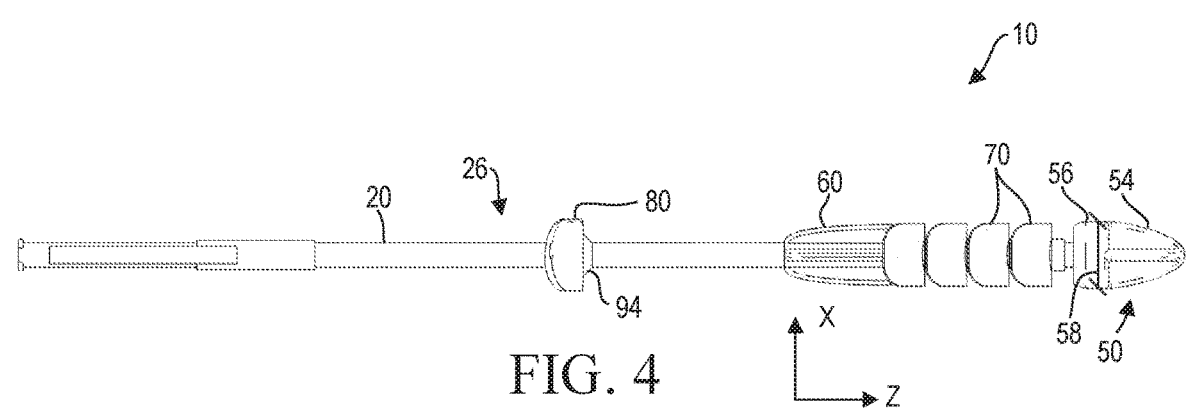
FIG. 4 is a side elevation view of the first fecal impaction removal device.

As is best seen in FIG. 3, the device 10 includes integrally formed reinforcement struts 72 that extend annularly about the shaft 20 and axially from the grappling elements 70. The reinforcement struts 72 may enhance structural stability of the grappling elements 70.

Once the device 10 has been inserted into the anus of a patient and manipulated to abduct the grappling elements 70 from a position folded toward and along the body of the shaft 20 (e.g., as is caused by insertion), the impacted fecal mass is engaged and manipulated through manual movement of the handle 30 by a practitioner. Such movements are translated along the shaft 20 to the opposite end of the device 10 carrying the dilators 50 and 60 as well as the sets of grappling elements 70. The length of the shaft 20 is chosen to be sufficient to efficiently permit insertion of the dilators 50 and 60 and the grappling elements 70 and to effectively transmit forces exerted on the handle 30 to the distal end of the device 10.

To limit the insertion length of the device 10, the device 10 includes an abutment member, also referred to herein as a stop member 80. The stop member 80 may be disposed at, and may extend from, a central region 26 of the shaft 20. In one non-limiting approach, the stop member is disposed in the range of approximately 120 millimeters to approximately 130 millimeters (e.g., 125 millimeters) from a proximal end surface of the device 10, and is disposed approximately in the range of approximately 130 millimeters to approximately 140 millimeters (e.g., 137 millimeters) from a distal end surface of the device 10.

The device 10 may be formed of a plastic material. In one aspect, shaft 20, the dilation body 50, and the stop member 80 are unitary and integrally formed, and may have a common, the shaft 20, the dilation body 50, and the stop member 80 have a common rigidity or hardness (e.g., a common shore "A" durometer value).

Figure 5:
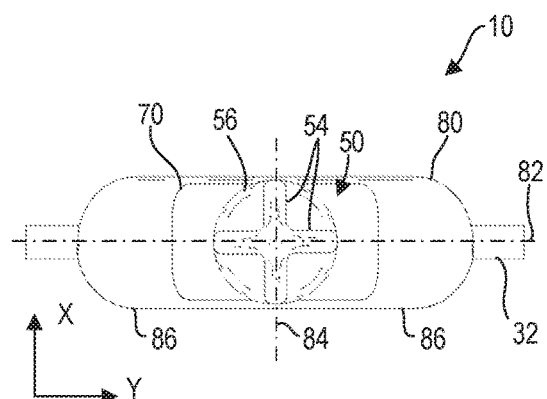
FIG. 5 is an enlarged front elevation view of the first fecal impaction removal device.
Figure 6:
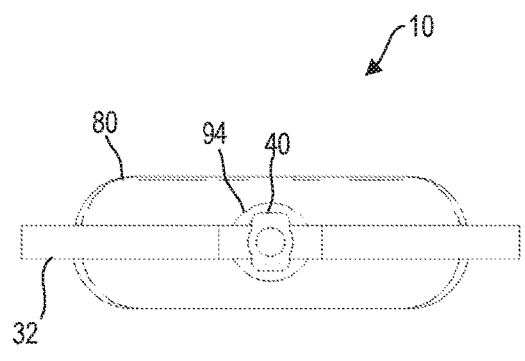
FIG. 6 is an enlarged rear elevation view of the first fecal impaction removal device.
Figures 7, 8:
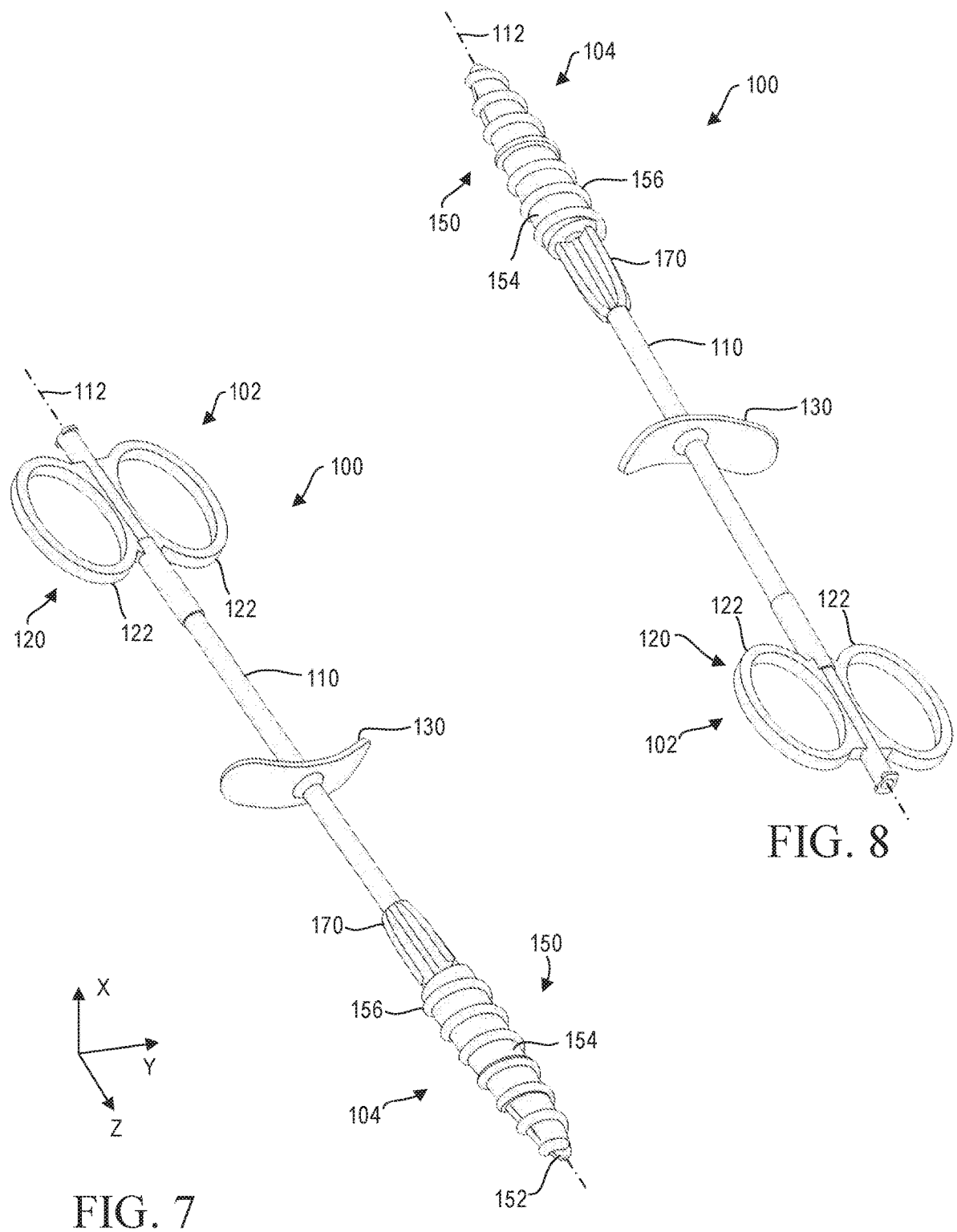
FIG. 7 is a perspective view of a second impaction removal device shown from a distal end.
FIG. 8 is a perspective view of the second fecal impaction removal device shown from a proximal end.
Figure 9:
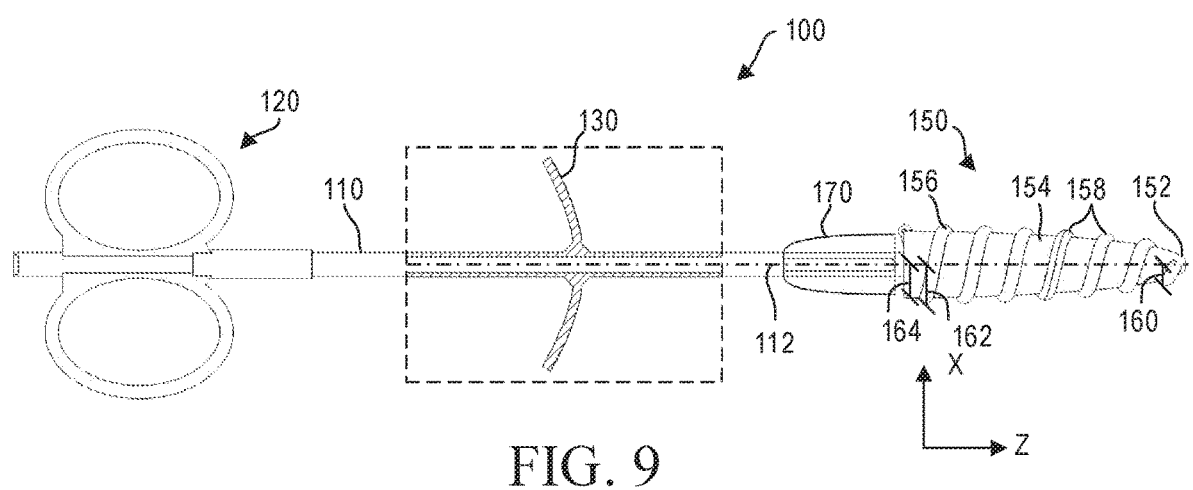
FIG. 9 is a side elevation view of the second fecal impaction removal device with a portion shown in cross-section.
Figure 10:
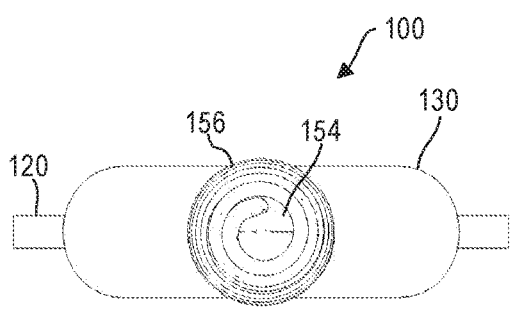
FIG. 10 is an enlarged front elevation view of the second fecal impaction removal device.
Figure 11:
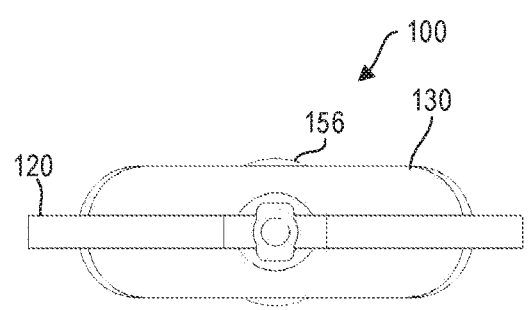
FIG. 11 is an enlarged rear elevation view of the second fecal impaction removal device.

As shown, the stop member 80 is a generally obround stop member. With reference momentarily to FIG. 5, the stop member 80 has a major central axis, referred to herein as major axis 82, and a minor central axis, referred to herein as minor axis 84 that extends generally orthogonal to the major central axis. In the approach shown, the stop member 80 includes fin portions 86 that generally extend in diametrically opposite directions. More particularly, the fin portions 86 extend from the central longitudinal axis 22 along the major axis 82 (e.g., in a direction parallel to the Y axis), and extend from the central longitudinal axis 22 along the minor axis 84 (e.g., in a direction parallel to the X axis).

The fin portions 86 extend a greater distance along the major axis 82 than along the minor axis 84. For example, in one approach, the fin portions 86 extend a first distance from the central longitudinal axis 22 along the minor axis 84, and extend a second distance from the central longitudinal axis 22 along the major axis 82 that may be at least two times the first distance, and more particularly, at least three times the first distance. As such, the length of the stop member 80 in a direction parallel to the Y axis may be greater than the height of the stop member 80 in a direction parallel to the X axis by at least a factor of two, and in some approaches, by at least a factor of three. In one non-limiting approach, the fin portions 86 extend approximately eight millimeters from the central longitudinal axis 22 along the minor axis 84 in opposing directions (e.g., parallel to the X axis), and extend approximately twenty three millimeters from the central longitudinal axis 22 along the major axis 82 in opposing directions (e.g., parallel to the Y axis).

Furthermore, the fin portions 86 may extend from the central longitudinal axis 22 along the minor axis 84 to a distance that generally corresponds to the maximum outer diameter 58 of the dilator 50. The fin portions 86 may extend from the central longitudinal axis 22 along the major axis 82 to a distance that is at least two times the maximum outer diameter 58 of the dilator 50, and more particularly, at least three times the maximum outer diameter 58 of the dilator 50. As such, the length of the stop member 80 in a direction parallel to the Y axis may be greater than the maximum outer diameter 58 of the dilator 50 by at least a factor of two, and in some approaches, by at least a factor of three.

Furthermore, the fin portions 86 may extend from the central longitudinal axis 22 along the major axis 82 to a distance that generally corresponds to, or is greater than, an extension of the grappling elements 70 in the same direction.

In still another approach, the stop member has an outer geometry that is not obround. For example, a stop member may have a generally circular outer geometry, or a generally polygonal (e.g., square or rectangular) outer geometry. In still another approach, the stop member may be in the form of a plurality of cross-members (e.g., in the form of an "X").

In one aspect, the stop member 80 is a curved stop member. More particularly, the stop member 80 curves generally away from the distal portion 14 and generally toward the proximal portion 12. In this way, the stop member 80 has a convex distal surface 90 that generally faces the dilation body 50, and a concave proximal surface 92 opposite the convex distal surface 90. The convex distal surface 90 and the concave proximal surface 92 generally curve in a direction (e.g., in a direction parallel to the Z axis) away from the dilation body 50 as the stop member extends radially away from the central longitudinal axis 22 (e.g., in a direction parallel to the Y axis). Due to the curvature of the stop member 80, the stop member 80 extends an axial distance along the central longitudinal axis 22. In one approach, the stop member 80 axial extends approximate eight millimeters to approximately nine millimeters along the central longitudinal axis 22. The stop member 80 may have a thickness of approximately two millimeters.

The device 10 may further include a base portion 94 that extends from the shaft 20 to the stop member 80. For example, as shown in FIG. 3, the base portion 94 is an annular base portion that extends about the shaft 20, and that tapers from the shaft 20 to opposing sides of the stop member 80. More particularly, a tapered distal portion of the base portion 94 extends from the shaft 20 to the convex distal surface 90, and a tapered proximal portion of the base portion 94 extends from the shaft 20 to the concave proximal surface 92. In one non-limiting approach, each of the tapered surfaces of the base portion 94 form an angle of approximately 135 degrees with the shaft 20, and extend axially approximately two millimeters along the central longitudinal axis 22.

The substantially hollow central channel 42 of the shaft 20 extends through the stop member 80. As such, the central channel 42 extends within the between the fin portions 86 and within the base portion 94.

Referring now to FIGS. 7-11, a fecal impaction removal device 100 includes a proximal portion 102 that a medical practitioner can grasp, and a distal portion 104 opposite the proximal portion 102 that is configured to be inserted through the anus of a patient and into the rectal vault to engage an impacted fecal mass lodged therein.

The fecal impaction removal device 100 includes a shaft 110, which may be an elongated shaft, that extends along a central axis 112 between the proximal portion 102 and the distal portion 104. The fecal impaction removal device 100 further includes a handle 120 at the proximal portion 102 of the device 100 (e.g., at a proximal end of the shaft 110). The handle 120 is formed of loops 122 that are each capable of receiving one or more of a practitioner's fingers for ease of use of the device 100.

To limit the insertion length of the device 100, the device 100 includes an abutment member, also referred to herein as a stop member 130. The stop member 130 may be disposed at, and may extend from, a central region of the shaft 110. One or more of the shaft 110, proximal portion 102, handle 120, and stop member 130 of the fecal impaction removal device 100 may generally correspond to those previously discussed with respect to the fecal impaction removal device 10 of FIGS. 1-6. As such, the various aspects of these components are not repeated for sake of brevity, but are incorporated with respect to FIGS. 7-9.

The shaft 110 terminates distally in a first or distal dilation body, also referred to herein as dilator 150. In one approach, the dilator 150 is formed integrally with the shaft 110. In another approach, the dilator 150 is separately formed and secured to the shaft 110.

The dilator 150 has a substantially elliptical or concave conformation with a rounded tip 152. The dilator 150 includes tapered portions, including a tapering body portion 154 and a tapering helical band 156 that extends about the tapering body portion 154 along the central axis 112. The tapering helical band 156 includes a curved or arcuate outer surface 158. In this way, interfaces between the tapering body portion 154 and the tapering helical band 156 are generally smooth interfaces.

Tapering portions of the dilator 100 (such as the tapering body portion 154 and the tapering helical band 156) may taper from a relatively close proximity to the central axis 112 at a distal portion of the dilator 150 (e.g., proximate the rounded tip 152), to a relatively increased proximity to the central axis at a proximal portion of the dilator 150. As such, the tapering body portion 154 has a varying outer diameter about the central axis 112 as the tapering portion 154 extends along the central axis 112. Similarly, the tapering helical band 156 has a varying outer diameter about the central axis 112 as the tapering helical band 156 extends along the central axis 112. More particularly, the tapering helical band 156 has a first radial extension 160 from the central longitudinal axis 122 at a distal end of the dilator 100, and a second radial extension 162 from the central longitudinal axis 122 at a proximal end of the dilator 100 that is greater than the first radial extension 160. In one aspect, the first radial height 160 of the tapering helical band 156 is less than a radial extension 164 of the tapering body portion 154 at the proximal end of the dilator 100.

The device 10 further includes a second or proximal dilation body, also referred to herein as dilator 170. In one approach, the dilator 170 is formed integrally with the shaft 110. In another approach, the dilator 170 is separately formed and secured to the shaft 110. The dilator 170 may generally correspond to the proximal dilator 60 previously discussed with respect to the fecal impaction removal device 10 of FIGS. 1-6.

Figures 12, 13:
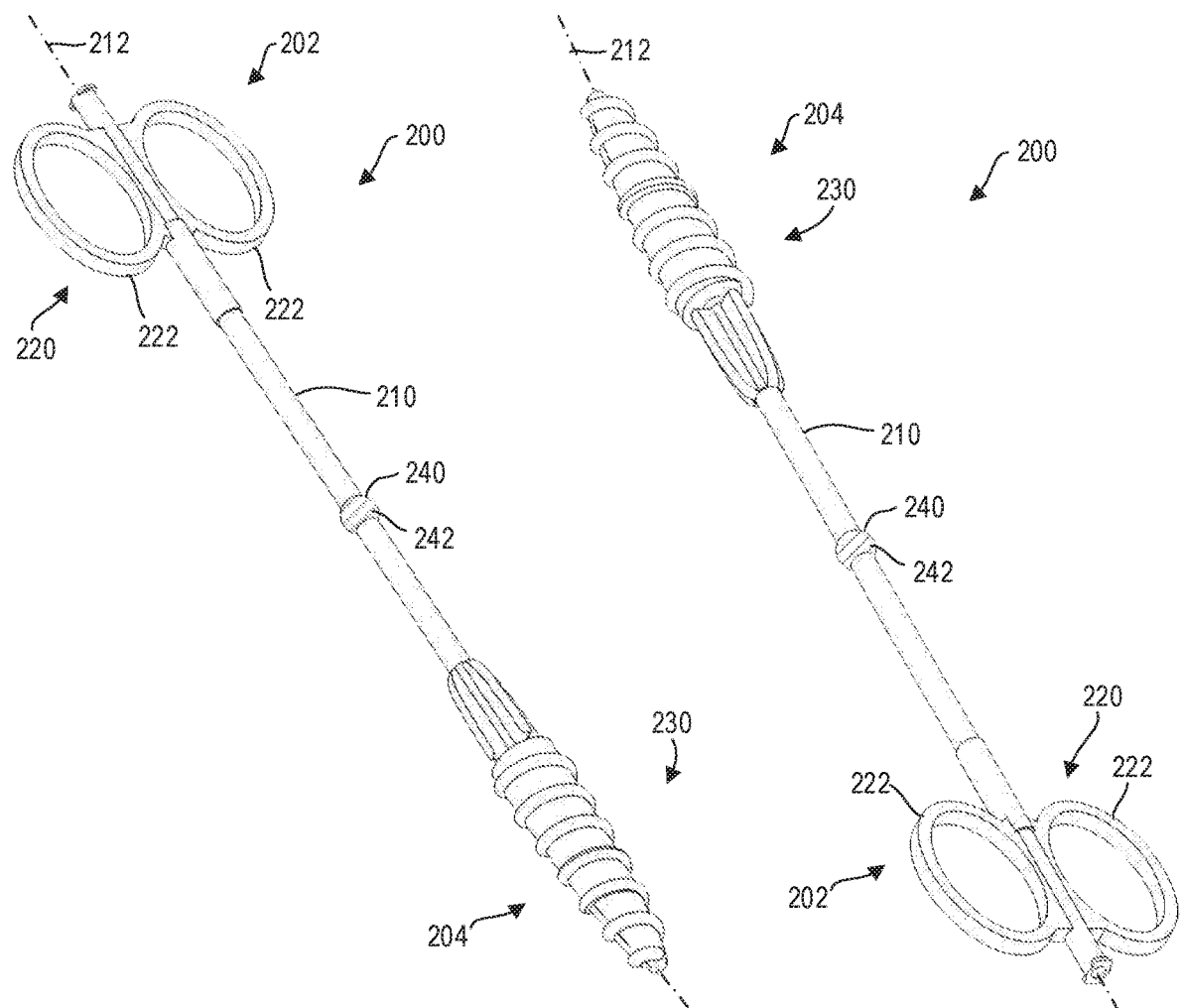
FIG. 12 is a perspective view of a third impaction removal device shown from a distal end.
FIG. 13 is a perspective view of the third fecal impaction removal device shown from a proximal end.
Figure 14:
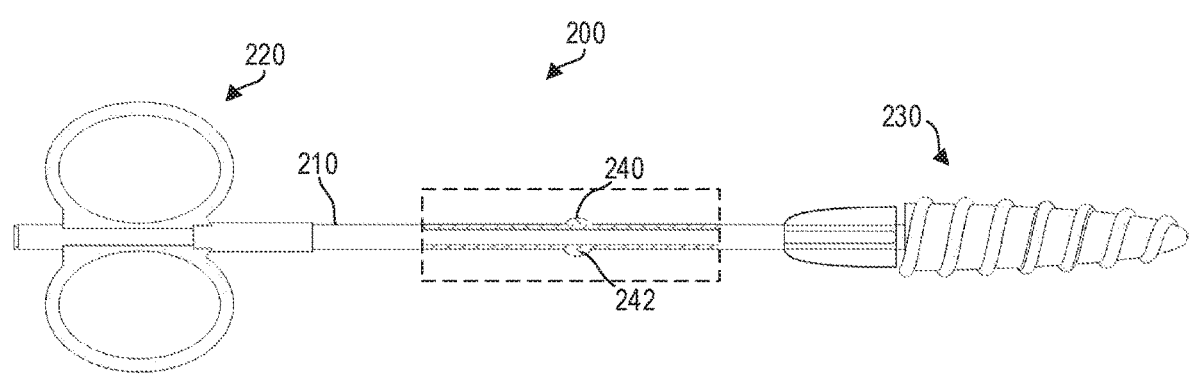
FIG. 14 is a side elevation view of the third fecal impaction removal device with a portion shown in cross-section.

Referring now to FIGS. 12-14, a fecal impaction removal device 200 includes a proximal portion 202 that a medical practitioner can grasp, and a distal portion 204 opposite the proximal portion 202 that is configured to be inserted through the anus of a patient and into the rectal vault to engage an impacted fecal mass lodged therein.

The fecal impaction removal device 200 includes a shaft 210, which may be an elongated shaft, that extends along a central axis 212 between the proximal portion 202 and the distal portion 204. The fecal impaction removal device 200 further includes a handle 220 at the proximal portion 202 of the device 200 (e.g., at a proximal end of the shaft 210). The handle 220 is formed of loops 222 that are each capable of receiving one or more of a practitioner's fingers for ease of use of the device 200.

The shaft 210 terminates distally in a first or distal dilation body, also referred to herein as dilator 230. In one approach, the dilator 230 is formed integrally with the shaft 210. In another approach, the dilator 230 is separately formed and secured to the shaft 210.

One or more of the shaft 210, proximal portion 202, and handle 220 of the fecal impaction removal device 200 may generally correspond to those previously discussed with respect to the fecal impaction removal device 10 of FIGS. 1-6. Furthermore, the dilator 230 may generally correspond to the dilator 150 previously discussed with respect to the fecal impaction removal device 100 of FIGS. 7-11. As such, the various aspects of these components are not repeated for sake of brevity, but are incorporated with respect to FIGS. 12-14.

To assist a practitioner in limiting the insertion length of the device 200, the device 200 includes an abutment member, also referred to herein as a depth indicator 240. The depth indicator 240 may be disposed at, and may extend about, a central region of the shaft 210. The depth indicator 240 may be, for example, in the form of a bulbous depth indicator. As such, the depth indicator 240 may be a generally spherical depth indicator that extends annularly about the central axis 212 of the shaft 210.

In one aspect, the bulbous depth indicator 240 is colored with an indicator color that is different than a color of the shaft 210, as indicated by shading 242. In this way, a practitioner is readily appraised of the depth of insertion of the distal portion 204 of the device 200 as the depth indicator 240 is moved in closer proximity to the patient. The indicator color could be printed on, stamped on, or stickered over the bulbous depth indicator 240. The indicator color may be any suitable indicator color, and in one approach, may be blue.

Figures 15, 16:
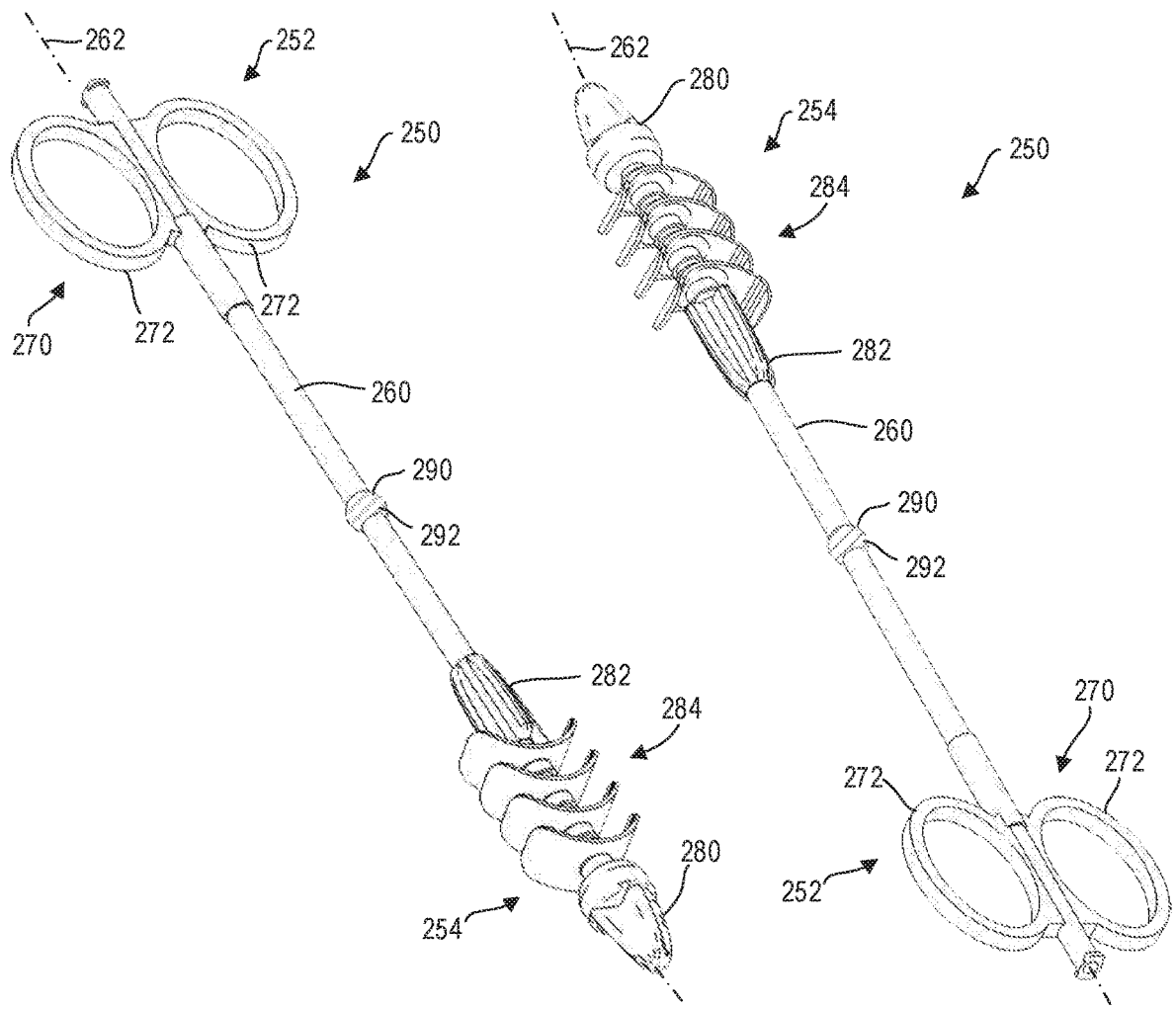
FIG. 15 is a perspective view of a fourth impaction removal device shown from a distal end.
FIG. 16 is a perspective view of the fourth fecal impaction removal device shown from a proximal end.
Figure 17:
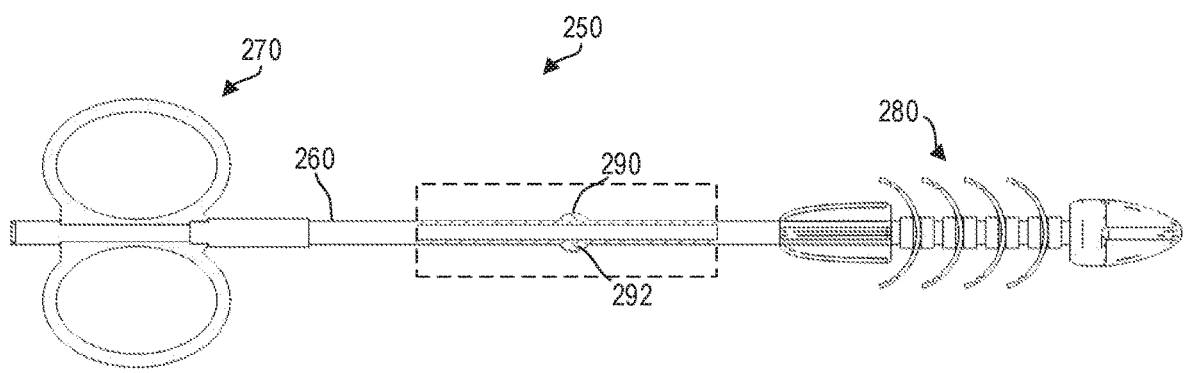
FIG. 17 is a side elevation view of the fourth fecal impaction removal device with a portion shown in cross-section.
Figure 22:
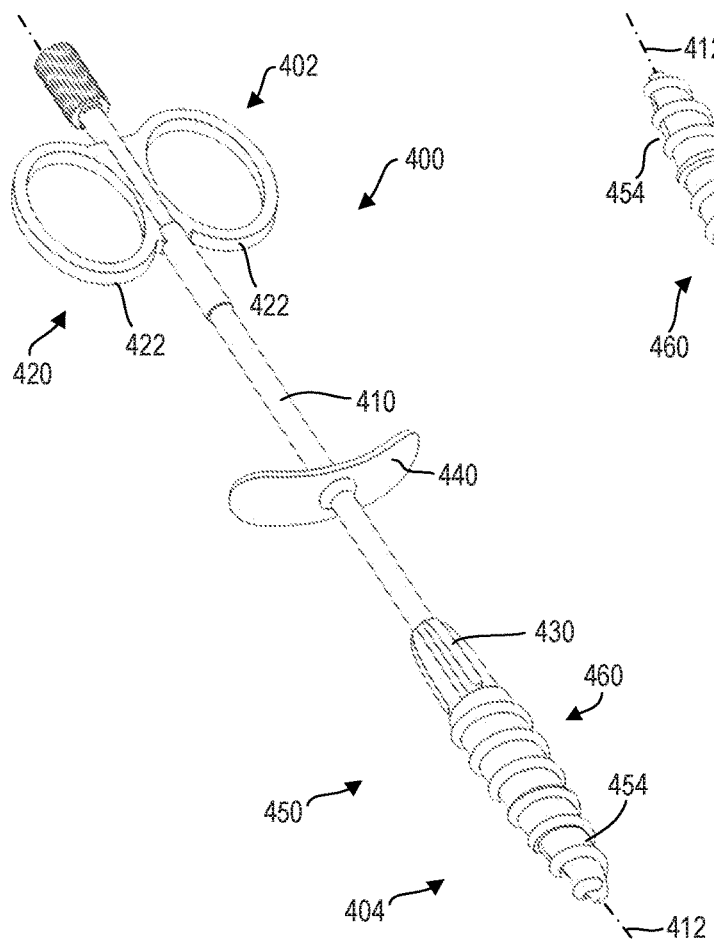
FIG. 22 is a perspective view of a sixth impaction removal device shown from a distal end.
Figure 23:
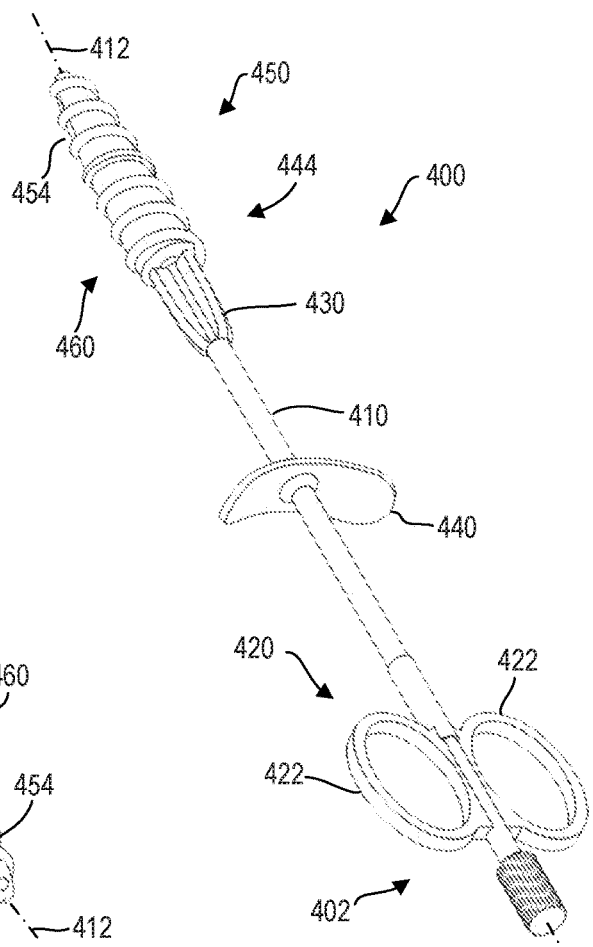
FIG. 23 is a perspective view of the sixth fecal impaction removal device shown from a proximal end.
Figure 24:
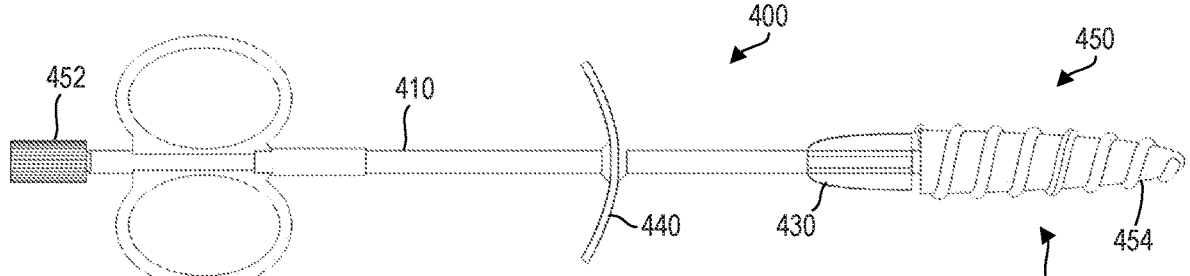
FIG. 24 is a side elevation view of the sixth fecal impaction removal device.

Referring now to FIGS. 15-17, a fecal impaction removal device 250 includes a proximal portion 252 that a medical practitioner can grasp, and a distal portion 254 opposite the proximal portion 252 that is configured to be inserted through the anus of a patient and into the rectal vault to engage an impacted fecal mass lodged therein.

The fecal impaction removal device 250 includes a shaft 260, which may be an elongated shaft, that extends along a central axis 262 between the proximal portion 252 and the distal portion 254. The fecal impaction removal device 250 further includes a handle 270 at the proximal portion 252 of the device 250 (e.g., at a proximal end of the shaft 260). The handle 270 is formed of loops 272 that are each capable of receiving one or more of a practitioner's fingers for ease of use of the device 250.

The shaft 260 terminates distally in a first or distal dilation body, also referred to herein as dilator 280. In one approach, the dilator 280 is formed integrally with the shaft 260. In another approach, the dilator 280 is separately formed and secured to the shaft 260.

A proximal dilator 282 is disposed in spaced relation to the distally disposed dilator 280. The device 250 further includes one or more grappling elements 284 disposed in spaced axial relation between the distally disposed dilator 280 and the proximal dilator 282.

One or more of the proximal portion 252, distal portion 254, shaft 260, handle 270, distal dilator 280, proximal dilator 282, and grappling elements 284 of the fecal impaction removal device 250 may generally correspond to those previously discussed with respect to the fecal impaction removal device 10 of FIGS. 1-6. As such, the various aspects of these components are not repeated for sake of brevity, but are incorporated with respect to FIGS. 15-17.

To assist a practitioner in limiting the insertion length of the device 250, the device 250 includes an abutment member, also referred to herein as a depth indicator 290, that may be colored with an indicator color that is different than a color of the shaft 260, as indicated by shading 292. The depth indicator 290 may generally correspond to the depth indicator 240 previously discussed with respect to the fecal impaction removal device 200 of FIGS. 12-14. As such, the various aspects of these components are not repeated for sake of brevity, but are incorporated with respect to FIGS. 15-17.

Referring now to FIGS. 18-21, a fecal impaction removal device 300 includes a proximal portion 302 that a medical practitioner can grasp, and a distal portion 304 opposite the proximal portion 302 that is configured to be inserted through the anus of a patient and into the rectal vault to engage an impacted fecal mass lodged therein.

The fecal impaction removal device 300 includes a shaft 310, which may be an elongated shaft, that extends along a central axis 312 between the proximal portion 302 and the distal portion 304. The fecal impaction removal device 300 further includes a handle 320 at the proximal portion 302 of the device 300 (e.g., at a proximal end of the shaft 310). The handle 320 is formed of loops 322 that are each capable of receiving one or more of a practitioner's fingers for ease of use of the device 300.

The shaft 310 terminates distally in a proximal dilation body, also referred to herein as dilator 330. In one approach, the dilator 330 is formed integrally with the shaft 310. In another approach, the dilator 330 is separately formed and secured to the shaft 310.

To limit the insertion length of the device 300, the device 300 includes an abutment member, also referred to herein as a stop member 340. The stop member 340 may be disposed at, and may extend from, a central region of the shaft 310. The stop member 340 may generally correspond to the stop member 80 of the fecal impaction removal device 10 of FIGS. 1-6.

The fecal impaction removal device 300 includes a rotatable body 350 that is rotatable about the central axis 312 relative to the shaft 310. The rotatable body 350 includes a knob 352, a distal dilator 354, and a rod 356 that extends between the knob 352 and the distal dilator 354. More particularly, the knob 352 is provided at the proximal portion 302 of the shaft 310. As best shown in FIG. 21, the rod 356 extends from the knob 352, and within and through the shaft 310. As such, the rod 354 extends between the loops 322 of the handle 320, through the stop member 340, and through the dilator 330.

The rotatable body 350 of the device 300 further includes one or more grappling elements 360 disposed in spaced axial relation between the distally disposed dilator 354 and the proximal dilator 330. The grappling elements 360 may generally correspond to those previously discussed with respect to the fecal impaction removal device 10 of FIGS. 1-6.

At least a portion of the rotatable body 350 is a single-piece member. For example, the knob 352 and the rod 356 may be unitary and integrally-formed to form a manipulation body 370. The dilator 354 and the grappling elements 360 may also be unitary and integrally-formed to form an insertion body 372. The insertion body 372 may be secured (e.g., rotatably fixed) to the manipulation body 370 such that rotation of the manipulation body 370 effects a corresponding rotation of the insertion body 372. In one approach, the insertion body 372 is threadedly secured to the manipulation body 370. In another approach, the insertion body 372 is welded (e.g., via ultrasonic welding) to the manipulation body 370.

In use, a practitioner may insert the insertion body 372 of the device 300 through the anus of a patient and into the rectal vault to engage an impacted fecal mass lodged therein. The handle 320, and more particularly, the loops 322 of the handle 320 may assist during insertion of the device 300. Upon insertion, the practitioner may operate the knob 352 to rotate the rod 356. As the insertion body 372 is rotatably fixed to the manipulation body 370, rotation of the knob 356 effects a corresponding rotation of the dilator 354 and grappling elements 360. Rotation of the insertion body 372 in engagement with the impacted fecal mass may assist in disimpacting the impacted fecal mass.

Referring now to FIGS. 22-25, a fecal impaction removal device 400 includes a proximal portion 402 that a medical practitioner can grasp, and a distal portion 404 opposite the proximal portion 402 that is configured to be inserted through the anus of a patient and into the rectal vault to engage an impacted fecal mass lodged therein.

The fecal impaction removal device 400 includes a shaft 410, which may be an elongated shaft, that extends along a central axis 412 between the proximal portion 402 and the distal portion 404. The fecal impaction removal device 400 further includes a handle 420 at the proximal portion 402 of the device 400 (e.g., at a proximal end of the shaft 410). The handle 420 is formed of loops 422 that are each capable of receiving one or more of a practitioner's fingers for ease of use of the device 400.

The shaft 410 terminates distally in a proximal dilation body, also referred to herein as dilator 430. In one approach, the dilator 430 is formed integrally with the shaft 410. In another approach, the dilator 430 is separately formed and secured to the shaft 410.

To limit the insertion length of the device 400, the device 400 includes an abutment member, also referred to herein as a stop member 440. The stop member 440 may be disposed at, and may extend from, a central region of the shaft 410. The stop member 440 may generally correspond to the stop member 80 of the fecal impaction removal device 10 of FIGS. 1-6.

Figure 25:
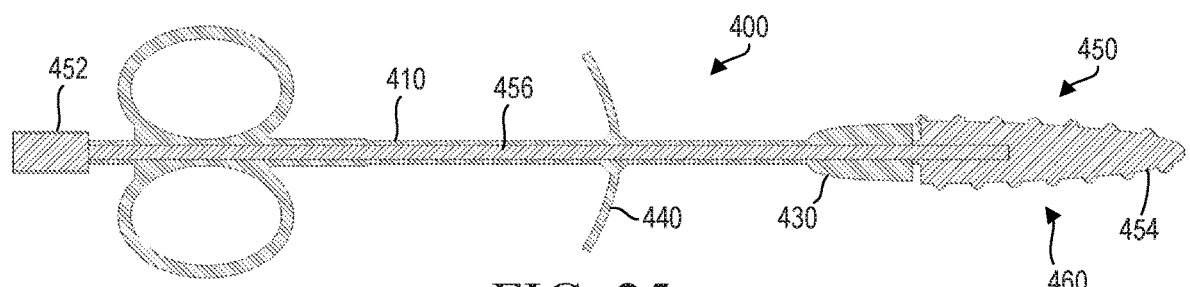
FIG. 25 is a side elevation cross-sectional view of the sixth fecal impaction removal device.
Figures 26, 27:
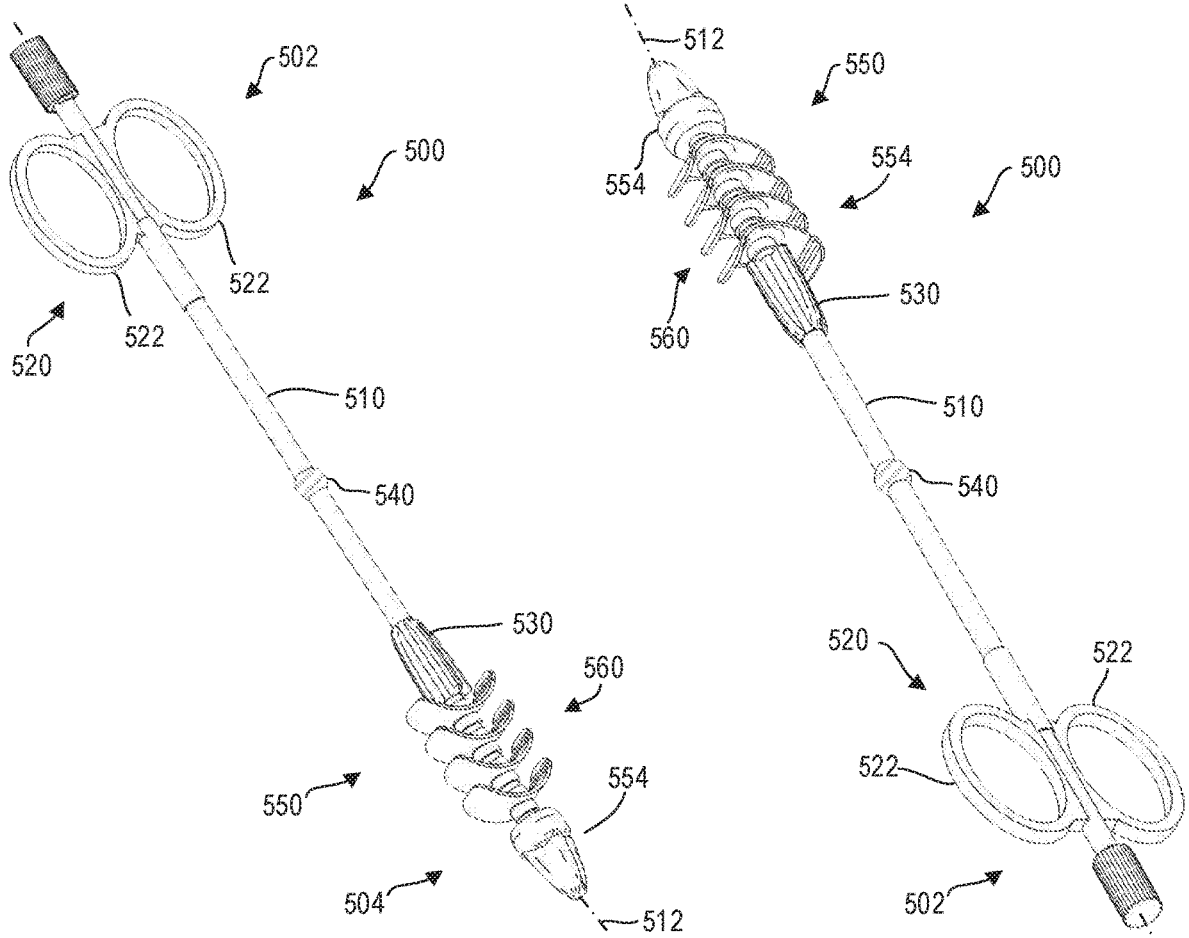
FIG. 26 is a perspective view of a seventh impaction removal device shown from a distal end.
FIG. 27 is a perspective view of the seventh fecal impaction removal device shown from a proximal end.
Figure 28:
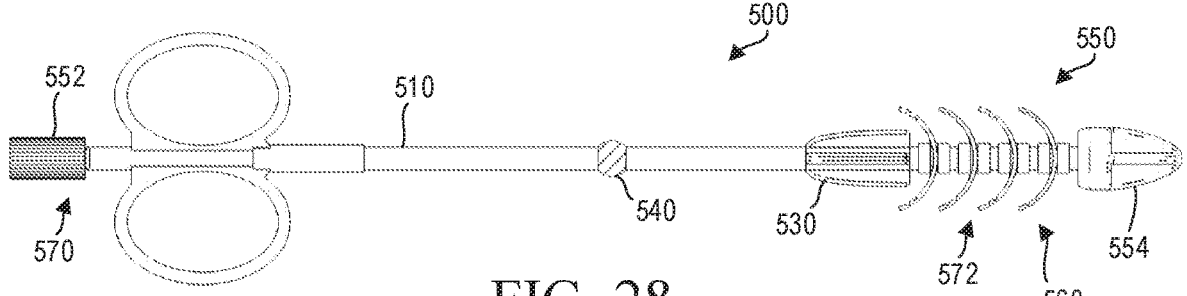
FIG. 28 is a side elevation view of the seventh fecal impaction removal device.

The fecal impaction removal device 400 includes a rotatable body 450 that is rotatable about the central axis 412 relative to the shaft 410. The rotatable body 450 includes a knob 452, a distal dilator 454, and a rod 456 that extends between the knob 452 and the distal dilator 454. More particularly, the knob 452 is provided at the proximal portion 402 of the shaft 410. As best shown in FIG. 25, the rod 456 extends from the knob 452, and within and through the shaft 410. As such, the rod 454 extends between the loops 422 of the handle 420, through the stop member 440, and through the dilator 430.

The dilator 454 may generally correspond to the dilator 150 previously discussed with respect to the fecal impaction removal device 100 of FIGS. 7-11. The dilator 454 may be secured (e.g., rotatably fixed) to the rod 456 such that rotation of the rod 456 effects a corresponding rotation of the dilator 454. In one approach, the dilator 454 is threadedly secured to the rod 456. In another approach, the dilator is welded (e.g., via ultrasonic welding) to the rod 456.

In use, a practitioner may insert the dilator 454 of the device 400 through the anus of a patient and into the rectal vault to engage an impacted fecal mass lodged therein. The handle 420, and more particularly, the loops 422 of the handle 420 may assist during insertion of the device 400. Upon insertion, the practitioner may operate the knob 452 to rotate the rod 456. As the dilator 454 is rotatably fixed to the rod 456, rotation of the knob 456 effects a corresponding rotation of the dilator 454. Rotation of the dilator 454 in engagement with the impacted fecal mass may assist in disimpacting the impacted fecal mass.

Referring now to FIGS. 26-29, a fecal impaction removal device 500 includes a proximal portion 502 that a medical practitioner can grasp, and a distal portion 504 opposite the proximal portion 502 that is configured to be inserted through the anus of a patient and into the rectal vault to engage an impacted fecal mass lodged therein.

The fecal impaction removal device 500 includes a shaft 510, which may be an elongated shaft, that extends along a central axis 512 between the proximal portion 502 and the distal portion 504. The fecal impaction removal device 500 further includes a handle 520 at the proximal portion 502 of the device 500 (e.g., at a proximal end of the shaft 510). The handle 520 is formed of loops 522 that are each capable of receiving one or more of a practitioner's fingers for ease of use of the device 500.

The shaft 510 terminates distally in a proximal dilation body, also referred to herein as dilator 530. In one approach, the dilator 530 is formed integrally with the shaft 510. In another approach, the dilator 530 is separately formed and secured to the shaft 510.

To limit the insertion length of the device 500, the device 500 includes an abutment member, also referred to herein as a stop member 540. The stop member 540 may be disposed at, and may extend from, a central region of the shaft 510. The stop member 540 may generally correspond to the stop member 80 of the fecal impaction removal device 10 of FIGS. 1-6.

To assist a practitioner in limiting the insertion length of the device 500, the device 500 includes an abutment member, also referred to herein as a depth indicator 540. The depth indicator 540 may be disposed at, and may extend about, a central region of the shaft 510. The depth indicator 540 may be, for example, in the form of a bulbous depth indicator. As such, the depth indicator 540 may be a generally spherical depth indicator that extends annularly about the central axis 512 of the shaft 510.

In one aspect, the bulbous depth indicator 540 is colored with an indicator color that is different than a color of the shaft 510. In this way, a practitioner is readily appraised of the depth of insertion of the distal portion 504 of the device 500 as the depth indicator 540 is moved in closer proximity to the patient.

Figure 29:
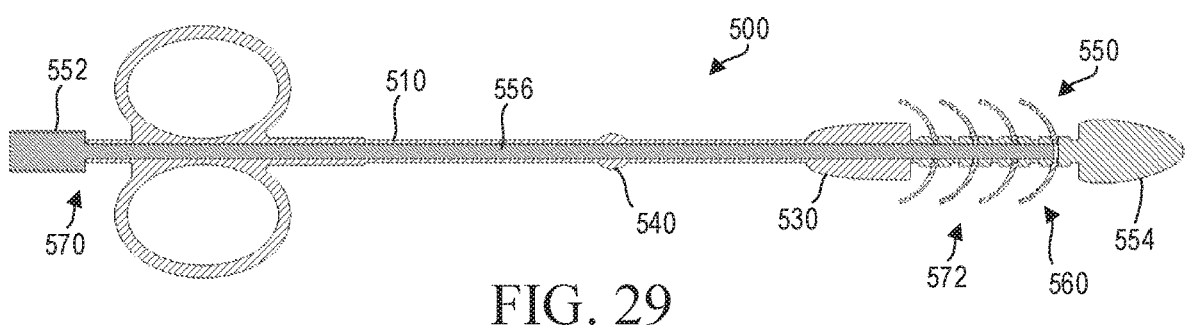
FIG. 29 is a side elevation cross-sectional view of the seventh fecal impaction removal device.
Figure 30:
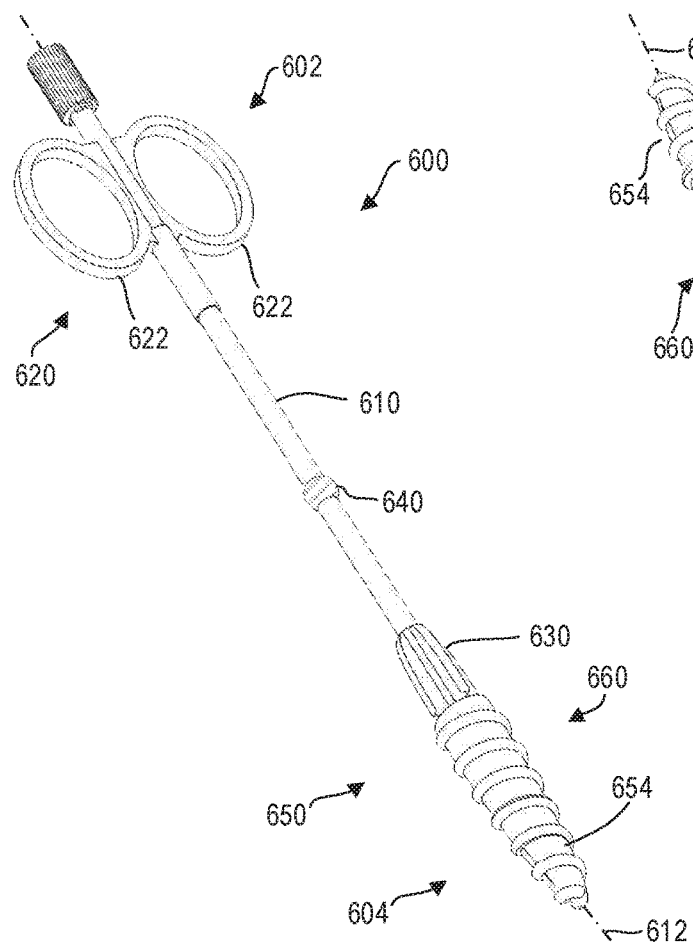
FIG. 30 is a perspective view of an eighth impaction removal device shown from a distal end.
Figure 31:
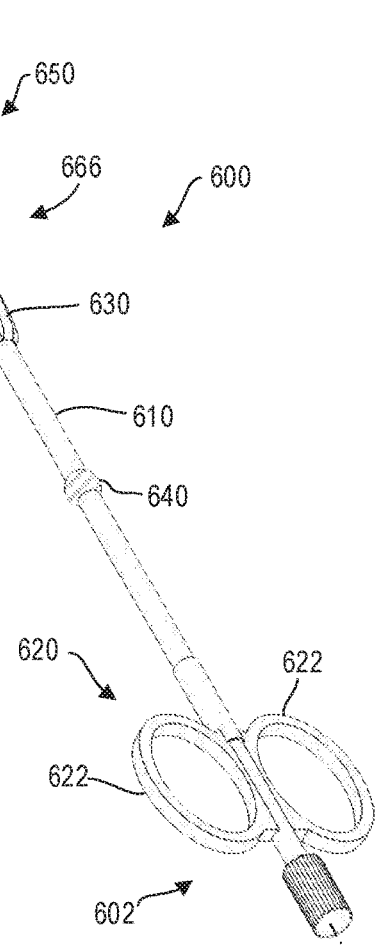
FIG. 31 is a perspective view of the eighth fecal impaction removal device shown from a proximal end.
Figure 32:
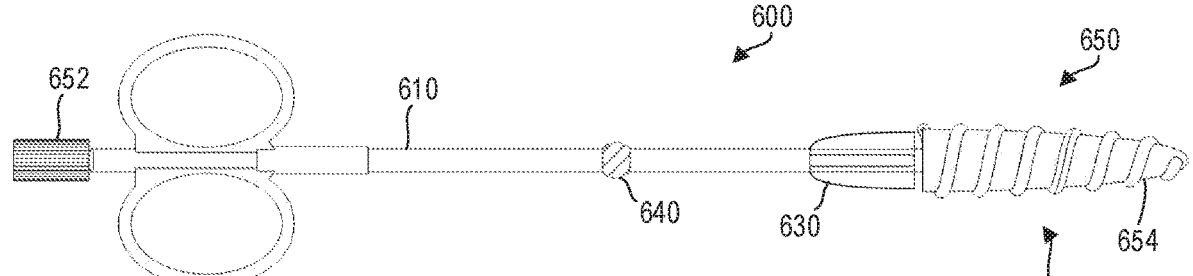
FIG. 32 is a side elevation view of the eighth fecal impaction removal device.

The fecal impaction removal device 500 includes a rotatable body 550 that is rotatable about the central axis 512 relative to the shaft 510. The rotatable body 550 includes a knob 552, a distal dilator 554, and a rod 556 that extends between the knob 552 and the distal dilator 554. More particularly, the knob 552 is provided at the proximal portion 502 of the shaft 510. As best shown in FIG. 29, the rod 556 extends from the knob 552, and within and through the shaft 510. As such, the rod 554 extends between the loops 522 of the handle 520, through the depth indicator 540, and through the dilator 530.

The rotatable body 550 of the device 500 further includes one or more grappling elements 560 disposed in spaced axial relation between the distally disposed dilator 554 and the proximal dilator 530. The grappling elements 560 may generally correspond to those previously discussed with respect to the fecal impaction removal device 10 of FIGS. 1-6.

At least a portion of the rotatable body 550 is a single-piece member. For example, the knob 552 and the rod 556 may be unitary and integrally-formed to form a manipulation body 570. The dilator 554 and the grappling elements 560 may also be unitary and integrally-formed to form an insertion body 572. The insertion body 572 may be secured (e.g., rotatably fixed) to the manipulation body 570 such that rotation of the manipulation body 570 effects a corresponding rotation of the insertion body 572. In one approach, the insertion body 572 is threadedly secured to the manipulation body 570. In another approach, the insertion body 572 is welded (e.g., via ultrasonic welding) to the manipulation body 570.

In use, a practitioner may insert the insertion body 572 of the device 500 through the anus of a patient and into the rectal vault to engage an impacted fecal mass lodged therein. The handle 520, and more particularly, the loops 522 of the handle 520 may assist during insertion of the device 500. Upon insertion, the practitioner may operate the knob 552 to rotate the rod 556. As the insertion body 572 is rotatably fixed to the manipulation body 570, rotation of the knob 556 effects a corresponding rotation of the dilator 554 and grappling elements 560. Rotation of the insertion body 572 in engagement with the impacted fecal mass may assist in disimpacting the impacted fecal mass.

Referring now to FIGS. 30-33, a fecal impaction removal device 600 includes a proximal portion 602 that a medical practitioner can grasp, and a distal portion 604 opposite the proximal portion 602 that is configured to be inserted through the anus of a patient and into the rectal vault to engage an impacted fecal mass lodged therein.

The fecal impaction removal device 600 includes a shaft 610, which may be an elongated shaft, that extends along a central axis 612 between the proximal portion 602 and the distal portion 604. The fecal impaction removal device 600 further includes a handle 620 at the proximal portion 602 of the device 600 (e.g., at a proximal end of the shaft 610). The handle 620 is formed of loops 622 that are each capable of receiving one or more of a practitioner's fingers for ease of use of the device 600.

The shaft 610 terminates distally in a proximal dilation body, also referred to herein as dilator 630. In one approach, the dilator 630 is formed integrally with the shaft 610. In another approach, the dilator 630 is separately formed and secured to the shaft 610.

To assist a practitioner in limiting the insertion length of the device 600, the device 600 includes an abutment member, also referred to herein as a depth indicator 640. The depth indicator 640 may be disposed at, and may extend about, a central region of the shaft 610. The depth indicator 640 may be, for example, in the form of a bulbous depth indicator. As such, the depth indicator 640 may be a generally spherical depth indicator that extends annularly about the central axis 612 of the shaft 610.

In one aspect, the bulbous depth indicator 640 is colored with an indicator color that is different than a color of the shaft 610. In this way, a practitioner is readily appraised of the depth of insertion of the distal portion 604 of the device 600 as the depth indicator 640 is moved in closer proximity to the patient.

Figure 33:
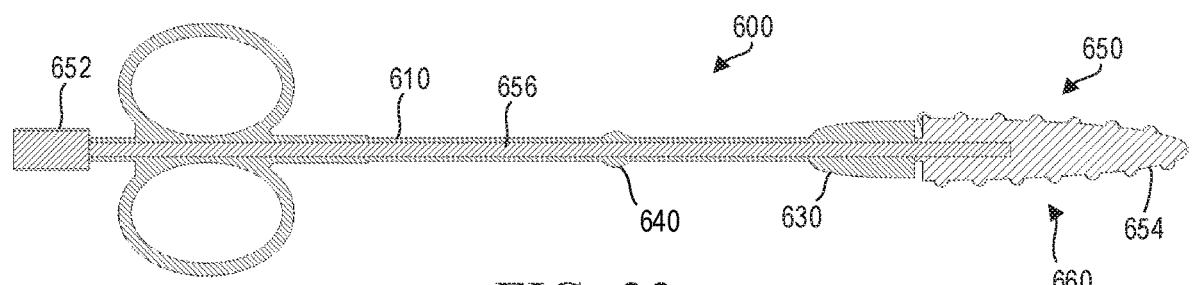
FIG. 33 is a side elevation cross-sectional view of the eighth fecal impaction removal device.

The fecal impaction removal device 600 includes a rotatable body 650 that is rotatable about the central axis 612 relative to the shaft 610. The rotatable body 650 includes a knob 652, a distal dilator 654, and a rod 656 that extends between the knob 652 and the distal dilator 654. More particularly, the knob 652 is provided at the proximal portion 602 of the shaft 610. As best shown in FIG. 33, the rod 656 extends from the knob 652, and within and through the shaft 610. As such, the rod 654 extends between the loops 622 of the handle 620, through the depth indicator 640, and through the dilator 630.

The dilator 654 may generally correspond to the dilator 150 previously discussed with respect to the fecal impaction removal device 100 of FIGS. 7-11. The dilator 654 may be secured (e.g., rotatably fixed) to the rod 656 such that rotation of the rod 656 effects a corresponding rotation of the dilator 654. In one approach, the dilator 654 is threadedly secured to the rod 656. In another approach, the dilator is welded (e.g., via ultrasonic welding) to the rod 656.

In use, a practitioner may insert the dilator 654 of the device 600 through the anus of a patient and into the rectal vault to engage an impacted fecal mass lodged therein. The handle 620, and more particularly, the loops 622 of the handle 620 may assist during insertion of the device 600. Upon insertion, the practitioner may operate the knob 652 to rotate the rod 656. As the dilator 654 is rotatably fixed to the rod 656, rotation of the knob 656 effects a corresponding rotation of the dilator 654. Rotation of the dilator 654 in engagement with the impacted fecal mass may assist in disimpacting the impacted fecal mass.

While exemplary embodiments are described above, it is not intended that these embodiments describe all possible forms encompassed by the claims. The words used in the specification are words of description rather than limitation, and it is understood that various changes may be made without departing from the spirit and scope of the disclosure. As previously described, the features of various embodiments may be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics may be compromised to achieve desired overall system attributes, which depend on the specific application and implementation. These attributes may include, but are not limited to cost, strength, durability, life cycle cost, marketability, appearance, packaging, size, serviceability, weight, manufacturability, ease of assembly, etc. As such, embodiments described as less desirable than other embodiments or prior art implementations with respect to one or more characteristics are not outside the scope of the disclosure and may be desirable for particular applications.

All methods described herein can be performed in any suitable order unless otherwise indicated herein or otherwise clearly contradicted by context. The use of any and all examples, or language describing an example (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. A fecal impaction removal device comprising:
   an elongated shaft that extends along a central longitudinal axis;
   a dilation body disposed at a distal portion of the elongated shaft for insertion into a rectum of a patient, the dilation body having a maximum radial extension in a direction orthogonal to the central longitudinal axis; and
   a stop member that extends from a central portion of the elongated shaft, the stop member having a length along a major axis that is greater than the maximum radial extension of the dilation body, wherein the stop member is a generally obround stop member that extends about the entire circumference of the elongated shaft and includes diametrically opposed fin portions that generally extend along the major axis.

2. The fecal impaction removal device of claim 1 further comprising a proximal dilator and a handle, the stop member being disposed axially between the proximal dilator and the handle.

3. The fecal impaction removal device of claim 1 further comprising a plurality of compressible grappling elements and a handle, the stop member being disposed axially between the compressible grappling elements and the handle.

4. The fecal impaction removal device of claim 3 wherein the length of the stop member along the major axis is greater than a length of an individual compressible grappling element.

5. The fecal impaction removal device of claim 1 wherein the length of the stop member is greater than the maximum radial extension of the dilation body by at least a factor of two.

6. The fecal impaction removal device of claim 1 wherein the elongated shaft, the dilation body, and the stop member have a common shore "A" durometer value.

7. The fecal impaction removal device of claim 1 wherein the dilation body is a tapered dilation body having a tapered surface and a tapering helical band that extends about the central longitudinal axis along the tapered surface.

8. The fecal impaction removal device of claim 1 wherein the elongated shaft includes a substantially hollow central channel that extends through the stop member.

9. The fecal impaction removal device of claim 1 wherein the elongated shaft, the dilation body, and the stop member are unitary and integrally formed.

10. A fecal impaction removal device comprising:
    an elongated shaft that extends along a central longitudinal axis;

a dilation body disposed at a distal end of the elongated shaft for insertion into a rectum of a patient, the dilation body including a tapering body portion and a tapering helical band that extends about tapering body portion along the central longitudinal axis; and an obround stopper disposed at a central region of the elongated shaft that extends about the entire circumference of the elongated shaft and includes diametrically opposed fin portions that curve away from the dilation body along the central longitudinal axis.

11. The fecal impaction removal device of claim 10 wherein the tapering helical band has a varying outer diameter about the central longitudinal axis as the tapering helical band extends along the central longitudinal axis.

12. The fecal impaction removal device of claim 10 wherein the tapering helical band has a first radial height from the central longitudinal axis at a distal end of the dilation body, and a second radial height from the central longitudinal axis at a proximal end of the dilation body, the second radial height greater than the first radial height.

13. The fecal impaction removal device of claim 12 wherein the first radial height of the tapering helical band is less than a radial height of the tapering body portion at the proximal end of the dilation body.

14. The fecal impaction removal device of claim 10 further comprising a bulbous depth indicator disposed at a central region of the elongated shaft, the bulbous depth indicator being colored an indicator color that is different than a color of the elongated shaft.

15. A fecal impaction removal device comprising:
an elongated shaft having a proximal portion, a distal portion opposite the proximal portion, and a substantially hollow central channel that extends along a central longitudinal axis between the proximal portion and the distal portion;

an actuating rod that extends through the central channel and is rotatable relative to the elongated shaft;

a tapered dilation body at a distal end of the actuating rod such that rotation of the actuating rod effects a rotation of the tapered dilation body relative to the elongated shaft, the tapered dilation body shaped for insertion into a rectum of a human; and a flexible grappling element between the tapered dilation body and the proximal portion of the elongated shaft and extending radially outwardly of the elongated shaft, the flexible grappling element rotatable with the tapered dilation body.

16. The fecal impaction removal device of claim 15 further comprising a stop member that extends from a central portion of the elongated shaft, the stop member having a length along a major axis that is greater than a maximum radial extension of the tapered dilation body.

17. The fecal impaction removal device of claim 15 wherein the dilation body includes a tapering body portion and a tapering helical band that extends about tapering body portion along the central longitudinal axis.

18. A fecal impaction removal device comprising:
an elongated shaft that extends along a central longitudinal axis;

a dilation body disposed at a distal portion of the elongated shaft for insertion into a rectum of a patient, the dilation body having a maximum radial extension in a direction orthogonal to the central longitudinal axis; and a stop member that extends from a central portion of the elongated shaft, the stop member having a length along a major axis that is greater than the maximum radial extension of the dilation body, wherein the stop member includes an annular base portion and symmetrical fins extending from the annular base portion.

* * * * *